United States Patent
Saito et al.

(10) Patent No.: US 11,500,043 B2
(45) Date of Patent: Nov. 15, 2022

(54) MAGNETOENCEPHALOGRAPH

(71) Applicants: HAMAMATSU PHOTONICS K.K., Hamamatsu (JP); Kyoto University, Kyoto (JP)

(72) Inventors: Akinori Saito, Hamamatsu (JP); Takahiro Moriya, Hamamatsu (JP); Takenori Oida, Hamamatsu (JP); Motohiro Suyama, Hamamatsu (JP); Tetsuo Kobayashi, Kyoto (JP)

(73) Assignees: HAMAMATSU PHOTONICS K.K., Hamamatsu (JP); Kyoto University, Kyoto (JP)

( * ) Notice: Subject to any disclaimer, the term of this patent is extended or adjusted under 35 U.S.C. 154(b) by 0 days.

(21) Appl. No.: 17/346,551

(22) Filed: Jun. 14, 2021

(65) Prior Publication Data

US 2021/0389397 A1 Dec. 16, 2021

(30) Foreign Application Priority Data

Jun. 16, 2020 (JP) .............................. JP2020-103931

(51) Int. Cl.
*G01R 33/26* (2006.01)
(52) U.S. Cl.
CPC .................................. *G01R 33/26* (2013.01)
(58) Field of Classification Search
CPC .. G01R 33/26; G01R 33/0094; G01R 33/032; A61B 5/245; A61B 5/246
See application file for complete search history.

(56) References Cited

U.S. PATENT DOCUMENTS

2021/0386347 A1* 12/2021 Moriya .................. G01R 33/26

FOREIGN PATENT DOCUMENTS

JP 5823195 B2 11/2015

OTHER PUBLICATIONS

Joonas Iivanainen et al., "On-scalp MEG system utilizing an actively shielded array of optically-pumped magnetometers", NeuroImage, 2019 vol. 194, p. 244-p. 258.
Elena Boto et al., "Moving magnetoencephalography towards real-world applications with a wearable system ", nature, Mar. 29, 2018 vol. 555.

* cited by examiner

*Primary Examiner* — Susan S Lee
(74) *Attorney, Agent, or Firm* — Faegre Drinker Biddle & Reath LLP

(57) ABSTRACT

A magnetoencephalograph M1 includes: multiple pump-probe type optically pumped magnetometers 1A; a bias magnetic field forming coil 15 for applying a bias magnetic field in the same direction as a direction of pump light of each of the multiple pump-probe type optically pumped magnetometers 1A and in a direction approximately parallel to a scalp; a control device 5 that determines a current for the bias magnetic field forming coil and outputs a control signal corresponding to the determined current; and a coil power supply 6 that outputs a current to the bias magnetic field forming coil in response to the control signal output from the control device.

8 Claims, 6 Drawing Sheets

MAGNETOENCEPHALOGRAPH

TECHNICAL FIELD

Aspects of the present invention relate to a magnetoencephalograph.

BACKGROUND

In the related art, as a magnetoencephalograph, a superconducting quantum interference device (SQUID) has been used to measure a small magnetic field of the brain. In recent years, a magnetoencephalograph using an optically pumped magnetometer instead of the SQUID has been studied. The optically pumped magnetometer measures a small magnetic field of the brain by using the spin polarization of alkali metal atoms excited by optical pumping. For example, Japanese Patent No. 5823195 discloses a magnetoencephalograph using an optically pumped magnetometer.

SUMMARY

Various types of optically pumped magnetometers, such as a uniaxial type and a pump-probe type, are known. The uniaxial optically pumped magnetometer has lower sensitivity than the pump-probe type optically pumped magnetometer. For this reason, the pump-probe type optically pumped magnetometer is desirable from the viewpoint of measuring the brain's magnetic field with high sensitivity. On the other hand, in the pump-probe type optically pumped magnetometer, in order to measure the brain's magnetic field with high accuracy, it is necessary to adjust the electron spin magnetic resonance frequency (hereinafter, referred to as resonance frequency) and the sensitivity band determined by the bias magnetic field applied in the pump light direction of the optically pumped magnetometer.

Aspects of the present invention have been made in view of the above circumstances, and it is an object of the present invention to provide a magnetoencephalograph capable of measuring the brain's magnetic field of the target frequency with high accuracy by appropriately adjusting the resonance frequency of a pump-probe type optically pumped magnetometer.

A magnetoencephalograph according to one aspect of the present invention includes: multiple pump-probe type optically pumped magnetometers that measure a brain's magnetic field; a bias magnetic field forming coil for applying a bias magnetic field in the same direction as a direction of pump light of each of the multiple pump-probe type optically pumped magnetometers and in a direction approximately parallel to a scalp; a control device that determines a current for the bias magnetic field forming coil so as to generate a bias magnetic field for adjusting resonance frequencies of the multiple pump-probe type optically pumped magnetometers to be included in a frequency band of the brain's magnetic field and outputs a control signal corresponding to the determined current; and a coil power supply that outputs a current to the bias magnetic field forming coil in response to the control signal output from the control device.

In the magnetoencephalograph according to one aspect of the present invention, the bias magnetic field is applied in the same direction as the direction of the pump light of each of the multiple pump-probe type optically pumped magnetometers and in the direction approximately parallel to the scalp, and the resonance frequencies of the multiple optically pumped magnetometers are adjusted to be included in the frequency band of the brain's magnetic field. Since the brain's magnetic field is generated in the direction approximately perpendicular to the scalp, the bias magnetic field can be applied in a direction suitable for the brain's magnetic field by applying the bias magnetic field in the direction approximately parallel to the scalp and in the same direction as the direction of the pump light. Then, in the magnetoencephalograph according to one aspect of the present invention, since the resonance frequencies of the multiple optically pumped magnetometers are adjusted to be included in the frequency band of the brain's magnetic field by the bias magnetic field, each of the multiple optically pumped magnetometers is adjusted to have a sensitivity suitable for measuring the brain's magnetic field. As described above, according to the magnetoencephalograph according to one aspect of the present invention, the brain's magnetic field can be measured with high accuracy by appropriately adjusting the resonance frequency of each optically pumped magnetometer.

A direction of the bias magnetic field may be a direction of each of concentric circles having a body axis of a subject as its center. Such a bias magnetic field in the direction of the concentric circles can be easily and stably generated. Since the bias magnetic field is stable, it is possible to stably measure the brain's magnetic field.

The bias magnetic field forming coil may be a coil system arranged so as to individually surround each of the multiple pump-probe type optically pumped magnetometers. According to such a configuration, a bias magnetic field is applied to each of the multiple optically pumped magnetometers. Therefore, a uniform bias magnetic field can be applied precisely.

The bias magnetic field forming coil may be a coil system arranged so as to surround at least two or more optically pumped magnetometers included in the multiple pump-probe type optically pumped magnetometers. According to such a configuration, the bias magnetic field is collectively applied to two or more optically pumped magnetometers surrounded by the bias magnetic field forming coil. Therefore, a uniform bias magnetic field can be efficiently applied with a simple configuration.

The multiple pump-probe type optically pumped magnetometers may be axial gradiometers having a measurement region and a reference region in a direction perpendicular to the scalp and coaxially. According to such a configuration, since the influence of common mode noise is shown in each of the output result of the measurement region and the output result of the reference region, the common mode noise can be removed by acquiring the difference between the output results of both. As a result, the measurement accuracy of the brain's magnetic field is improved.

The magnetoencephalograph according to one aspect of the present invention may further include: multiple magnetic sensors for geomagnetic field correction that measure a geomagnetic field at a position of each of the multiple pump-probe type optically pumped magnetometers; multiple magnetic sensors for active magnetic shield that measure a fluctuating magnetic field at the position of each of the multiple pump-probe type optically pumped magnetometers; a geomagnetic field correction coil for correcting the geomagnetic field; and an active magnetic shield coil for correcting the fluctuating magnetic field. The control device may determine a current for the geomagnetic field correction coil so as to generate a magnetic field for canceling the geomagnetic field based on measured values of the multiple magnetic sensors for geomagnetic field correction, determine a current for the active magnetic shield coil so as to generate a magnetic field for canceling the fluctuating magnetic field based on measured values of the multiple magnetic sensors for active magnetic shield, and output a control signal corresponding to each of the determined currents. The coil power supply may further output a current to each of the geomagnetic field correction coil and the active magnetic shield coil in response to the control signal output from the control device. According to such a configuration, the geomagnetic field and the fluctuating magnetic field at the position of each of the multiple optically pumped magnetometers for measuring the brain's magnetic field are measured. Then, in this magnetoencephalograph, the current for the geomagnetic field correction coil is determined so as to generate a magnetic field for canceling the geomagnetic field based on the multiple measured values of the geomagnetic field, the current for the active magnetic shield coil is determined so as to generate a magnetic field for canceling the fluctuating magnetic field based on the multiple measured values of the fluctuating magnetic field, and the control signal corresponding to each of the determined currents is output. Then, when the current corresponding to the control signal is output to each of the geomagnetic field correction coil and the active magnetic shield coil, a magnetic field is generated in each coil. At the positions of the multiple optically pumped magnetometers, the geomagnetic field is canceled by the magnetic field generated in the geomagnetic field correction coil, and the fluctuating magnetic field is canceled by the magnetic field generated in the active magnetic shield coil. Therefore, since the geomagnetic field and the fluctuating magnetic field at the positions of the multiple optically pumped magnetometers are canceled, the multiple optically pumped magnetometers can measure the brain's magnetic field in a state in which the influence of the geomagnetic field and the influence of the fluctuating magnetic field are avoided. According to such a magnetoencephalograph, the brain's magnetic field can be measured with high accuracy without using the magnetic shield room.

The multiple pump-probe type optically pumped magnetometers, the multiple magnetic sensors for geomagnetic field correction, and the multiple magnetic sensors for active magnetic shield may be fixed to a non-magnetic frame which is a helmet-type frame attached to a head of a subject and whose relative permeability is close to 1 so that a magnetic field distribution is not affected. According to such a configuration, the non-magnetic frame attached to the head and each sensor fixed to the non-magnetic frame move according to the movement of the head of the subject. Therefore, even when the head of the subject moves, it is possible to appropriately correct the geomagnetic field and the fluctuating magnetic field at the positions of the multiple optically pumped magnetometers and measure the brain's magnetic field.

The magnetoencephalograph according to one aspect of the present invention may further include an electromagnetic shield for shielding high-frequency electromagnetic noise. According to such a configuration, it is possible to prevent high-frequency electromagnetic noise, which cannot be measured by the magnetoencephalograph, from entering the multiple optically pumped magnetometers. As a result, the multiple optically pumped magnetometers can be stably operated.

According to aspects of the present invention, it is possible to provide a magnetoencephalograph capable of performing measurement with high accuracy by adjusting resonance frequencies of multiple pump-probe type optically pumped magnetometers to frequencies of the desired brain's magnetic field.

DETAILED DESCRIPTION

Figure 1:
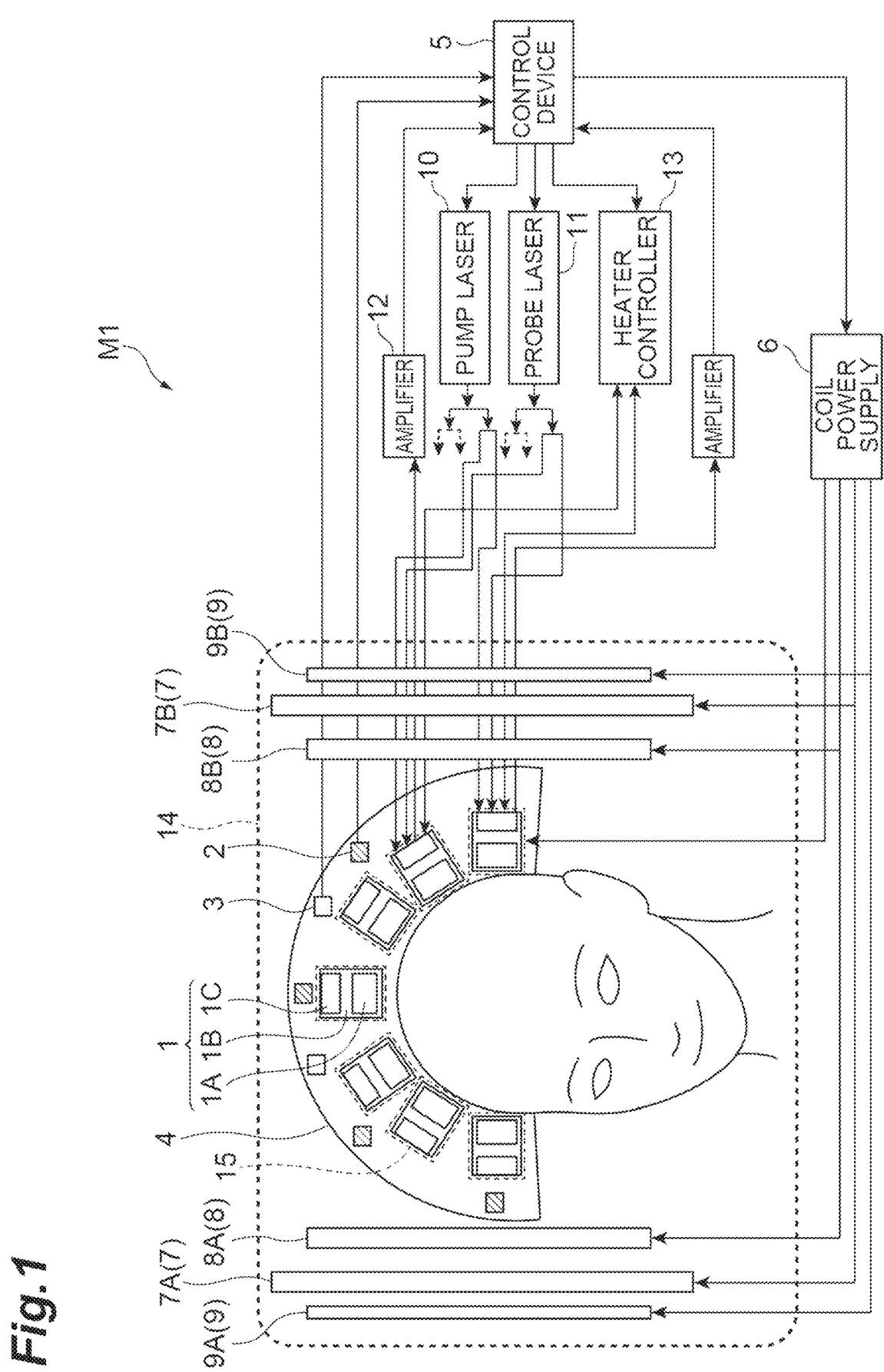
FIG. 1 is a schematic diagram showing the configuration of a magnetoencephalograph according to an embodiment.

Hereinafter, an embodiment for carrying out the present invention will be described in detail with reference to the accompanying diagrams. In the description of the diagrams, the same elements are denoted by the same reference numerals, and the repeated description thereof will be omitted.

FIG. 1 is a schematic diagram showing the configuration of a magnetoencephalograph M1 according to an embodiment. The magnetoencephalograph M1 is an apparatus that measures a magnetic field of the brain by using optical pumping while generating a magnetic field that cancels magnetic noise. The magnetoencephalograph M1 includes multiple optically pumped magnetometer (OPM) modules 1, multiple magnetic sensors for geomagnetic field correction 2, multiple magnetic sensors for active magnetic shield 3, a non-magnetic frame 4, a control device 5, a coil power supply 6, a pair of geomagnetic field correction coils 7, a pair of gradient magnetic field correction coils 8 (geomagnetic field correction coils), a pair of active magnetic shield coils 9, a pump laser 10, a probe laser 11, an amplifier 12, a heater controller 13, an electromagnetic shield 14, and a bias magnetic field forming coil 15.

Each OPM module 1 includes a pump-probe type optically pumped magnetometer 1A, a heat insulating material 1B, and a read circuit 1C. The multiple OPM modules 1 are arranged at predetermined intervals along the scalp, for example.

The optically pumped magnetometer 1A is a sensor that measures a brain's magnetic field by using optical pumping, and has a sensitivity of, for example, about 10 fT to 10 pT. The heat insulating material 1B prevents heat transfer of the optically pumped magnetometer 1A heated to 180° by a heater (not shown). The read circuit 1C is a circuit for acquiring the detection result of the optically pumped magnetometer 1A. The pump laser 10 emits pump light to a cell containing alkali metal vapor to excite the alkali metal vapor. The excited alkali metal vapor is in a spin polarization state, and when this receives magnetic field, the inclination of the spin polarization axis of the alkali metal vapor changes according to the magnetic field. Then, the linearly polarized light plane rotates according to the magnitude of a component in the probe light direction emitted in a direction perpendicular to the pump light of the spin polarization. In order to detect the rotation angle (magnetic rotation angle), the read circuit 1C receives probe light passing through the alkali metal vapor by a photodiode and acquires the detection result. The read circuit 1C outputs the detection result to the amplifier 12.

The optically pumped magnetometer 1A may be, for example, an axial gradiometer. The axial gradiometer has a measurement region and a reference region in a direction perpendicular to the scalp (measurement location) of the subject and coaxially. The measurement region is, for example, a location closest to the scalp of the subject among locations where the axial gradiometer measures the brain's magnetic field. The reference region is, for example, a location away from the measurement region by a predetermined distance (for example, 3 cm) in a direction away from the scalp of the subject, among locations where the axial gradiometer measures the brain's magnetic field. The axial gradiometer outputs the respective measurement results in the measurement region and the reference region to the amplifier 12. Here, when common mode noise is included, its influence is shown in each of the output result of the measurement region and the output result of the reference region. Common mode noise is removed by acquiring the difference between the output result of the measurement region and the output result of the reference region. By removing the common mode noise, the optically pumped magnetometer 1A can obtain a sensitivity of about 10 fT/√Hz, for example, when performing measurement in a magnetic noise environment of 1 pT.

The magnetic sensor for geomagnetic field correction 2 is a sensor that measures a geomagnetic field at a position corresponding to the optically pumped magnetometer 1A, and is, for example, a flux gate sensor having a sensitivity of about 1 nT to 100 μT. The position corresponding to the optically pumped magnetometer 1A is a position around (near) the region where the optically pumped magnetometer 1A is arranged. The magnetic sensor for geomagnetic field correction 2 may be provided so as to correspond to the optically pumped magnetometer 1A in a one-to-one manner, or may be provided so as to correspond in a one-to-many manner (one magnetic sensor for geomagnetic field correction 2 for multiple optically pumped magnetometers 1A). The magnetic sensor for geomagnetic field correction 2 measures, for example, geomagnetism and a gradient magnetic field of the geomagnetism (hereinafter, simply referred to as "gradient magnetic field") as magnetic fields relevant to the geomagnetism, and outputs the measured value to the control device 5. The measured value of the magnetic sensor for geomagnetic field correction 2 can be expressed by a vector having a direction and a magnitude. The magnetic sensor for geomagnetic field correction 2 may continuously perform measurement and output at predetermined time intervals.

The magnetic sensor for active magnetic shield 3 is a sensor that measures a fluctuating magnetic field at a position corresponding to the optically pumped magnetometer 1A, and is, for example, a optically pumped magnetometer having a sensitivity of about 100 fT to 10 nT in a frequency band of several hundred Hz or less and different from the optically pumped magnetometer 1A. The position corresponding to the optically pumped magnetometer 1A is a position around (near) the region where the optically pumped magnetometer 1A is arranged. The magnetic sensor for active magnetic shield 3 may be provided so as to correspond to the optically pumped magnetometer 1A in a one-to-one manner, or may be provided so as to correspond in a one-to-many manner (one magnetic sensor for active magnetic shield 3 for the multiple optically pumped magnetometers 1A). The magnetic sensor for active magnetic shield 3 measures a magnetic field of a noise (AC) component of, for example, 200 Hz or less as a fluctuating magnetic field, and outputs the measured value to the control device 5. The measured value of the magnetic sensor for active magnetic shield 3 can be expressed by a vector having a direction and a magnitude.

The non-magnetic frame 4 is a frame that covers the entire scalp of the subject whose brain's magnetic field is to be measured, and is formed of a non-magnetic material such as graphite whose relative permeability is close to 1 and accordingly does not affect the magnetic field distribution. The non-magnetic frame 4 can be, for example, a helmet-type frame that surrounds the entire scalp of the subject and is attached to the head of the subject. The multiple optically pumped magnetometers 1A are fixed to the non-magnetic frame 4 so as to be close to the scalp of the subject. In addition, the magnetic sensor for geomagnetic field correction 2 is fixed to the non-magnetic frame 4 so that a geomagnetic field at the position of each of the multiple optically pumped magnetometers 1A can be measured, and the magnetic sensor for active magnetic shield 3 is fixed to the non-magnetic frame 4 so that a fluctuating magnetic field at the position of each of the multiple optically pumped magnetometers 1A can be measured. Since a change in the magnetic field strength according to the position of the fluctuating magnetic field is smaller than that in the case of the static magnetic field, a smaller number of magnetic sensors for active magnetic shield 3 than the number of magnetic sensors for geomagnetic field correction 2 may be fixed to the non-magnetic frame 4.

The control device 5 is a device that determines currents for various coils based on the measured values output from the magnetic sensor for geomagnetic field correction 2 and the magnetic sensor for active magnetic shield 3, and outputs a control signal for outputting each of the currents to the coil power supply 6. Based on the measured values of the multiple magnetic sensors for geomagnetic field correction 2, the control device 5 determines a current for the geomagnetic field correction coil 7 and the gradient magnetic field correction coil 8, which are geomagnetic field correction coils, so as to generate a magnetic field for canceling a geomagnetic field. In addition, based on the measured values of the multiple magnetic sensors for active magnetic shield 3, the control device 5 determines a current for the active magnetic shield coil 9 so as to generate a magnetic field for canceling a fluctuating magnetic field. The control device 5 determines a current for the bias magnetic field forming coil 15 so as to generate a bias magnetic field for adjusting the resonance frequencies of the multiple pump-probe type optically pumped magnetometers 1A to be included in the frequency band of the brain's magnetic field. The control device 5 outputs a control signal corresponding to the determined current to the coil power supply 6.

Specifically, the control device 5 determines a current for the geomagnetic field correction coil 7 so that the average value of the measured values of the multiple magnetic sensors for geomagnetic field correction 2 approaches zero (as a result, a magnetic field opposite to the geomagnetism at the position of the optically pumped magnetometer 1A and having approximately the same magnitude as the geomagnetism is generated). The control device 5 outputs a control signal (control signal for static magnetic field correction) corresponding to the determined current of the geomagnetic field correction coil 7 from the coil power supply 6.

In addition, the control device 5 determines a current for the gradient magnetic field correction coil 8 so that the deviation from the average value of the measured values of the multiple magnetic sensors for geomagnetic field correction 2 is minimized (as a result, a magnetic field opposite to the gradient magnetic field at the position of the optically pumped magnetometer 1A and having approximately the same magnitude as the gradient magnetic field is generated). The control device 5 outputs a control signal (control signal for static magnetic field correction) corresponding to the determined current of the gradient magnetic field correction coil 8 from the coil power supply 6.

In addition, the control device 5 determines a current for the active magnetic shield coil 9 so that the average value of the measured values of the multiple magnetic sensors for active magnetic shield 3 approaches zero (as a result, a magnetic field opposite to the fluctuating magnetic field at the position of the optically pumped magnetometer 1A and having approximately the same magnitude as the fluctuating magnetic field is generated). The control device 5 outputs a control signal (control signal for fluctuating magnetic field correction) corresponding to the determined current of the active magnetic shield coil 9 from the coil power supply 6.

In addition, the control device 5 determines a current for the bias magnetic field forming coil 15 so that the resonance frequencies of the multiple pump-probe type optically pumped magnetometers 1A are frequencies included in the frequency band (for example, between several to several hundred Hz) of the brain's magnetic field. In particular, when selectively measuring a β wave of about 16 to 30 Hz, a γ wave of about 40 to 80 Hz, a high-γ wave of about several hundred Hz, or the like, the control device 5 determines a current for the bias magnetic field forming coil 15 so as to form the bias magnetic fields of 3.6 nT, 8.6 nT, and 28.5 nT so that the resonance frequency is included in each frequency band. The control device 5 outputs a control signal (control signal for bias magnetic field application) corresponding to the determined current of the bias magnetic field forming coil 15 from the coil power supply 6.

In addition, the control device 5 obtains information regarding the magnetic field detected by the optically pumped magnetometer 1A by using the signal output from the amplifier 12. When the optically pumped magnetometer 1A is an axial gradiometer, the control device 5 may remove the common mode noise by acquiring the difference between the output result of the measurement region and the output result of the reference region. In addition, the control device 5 may control operations such as the emission timing and the emission time of the pump laser 10 and the probe laser 11.

The control device 5 is physically configured to include a memory such as a RAM and a ROM, a processor (arithmetic circuit) such as a CPU, a communication interface, and a storage unit such as a hard disk. Examples of the control device 5 include a personal computer, a cloud server, a smartphone, and a tablet terminal. The control device 5 functions by executing a program stored in the memory on the CPU of the computer system.

The coil power supply 6 outputs a predetermined current to each of the geomagnetic field correction coil 7, the gradient magnetic field correction coil 8, the active magnetic shield coil 9, and the bias magnetic field forming coil 15 in response to the control signal output from the control device 5. Specifically, the coil power supply 6 outputs a current to the geomagnetic field correction coil 7 in response to the control signal relevant to the geomagnetic field correction coil 7. The coil power supply 6 outputs a current to the gradient magnetic field correction coil 8 in response to the control signal relevant to the gradient magnetic field correction coil 8. The coil power supply 6 outputs a current to the active magnetic shield coil 9 in response to the control signal relevant to the active magnetic shield coil 9. The coil power supply 6 outputs a current to the bias magnetic field forming coil 15 in response to the control signal relevant to the bias magnetic field forming coil 15.

The geomagnetic field correction coil 7 is a coil for correcting the magnetic field of the geomagnetism among the magnetic fields relevant to the geomagnetism at the position of the optically pumped magnetometer 1A. The geomagnetic field correction coil 7 generates a magnetic field according to the current supplied from the coil power supply 6 to cancel the geomagnetism. The geomagnetic field correction coil 7 has, for example, a pair of geomagnetic field correction coils 7A and 7B. The pair of geomagnetic field correction coils 7A and 7B are arranged with the optically pumped magnetometer 1A interposed therebetween (for example, on the left and right of the subject). The pair of geomagnetic field correction coils 7A and 7B generate a magnetic field, which is opposite to the geomagnetism at the position of the optically pumped magnetometer 1A and has approximately the same magnitude as the geomagnetism, according to the current supplied from the coil power supply 6. The direction of the magnetic field is, for example, from one geomagnetic field correction coil 7A to the other geomagnetic field correction coil 7B. The geomagnetism at the position of the optically pumped magnetometer 1A is canceled by a magnetic field generated by the geomagnetic field correction coil 7, the magnetic field being opposite to the geomagnetism and having approximately the same magnitude as the geomagnetism. In this manner, the geomagnetic field correction coil 7 corrects the geomagnetism at the position of the optically pumped magnetometer 1A.

The gradient magnetic field correction coil 8 is a coil for correcting the gradient magnetic field among the magnetic fields relevant to the geomagnetism at the position of the optically pumped magnetometer 1A. The gradient magnetic field correction coil 8 generates a magnetic field according to the current supplied from the coil power supply 6 to cancel the gradient magnetic field. The gradient magnetic field correction coil 8 has, for example, a pair of gradient magnetic field correction coils 8A and 8B. The pair of gradient magnetic field correction coils 8A and 8B are arranged with the optically pumped magnetometer 1A interposed therebetween (for example, on the left and right of the subject). The pair of gradient magnetic field correction coils 8A and 8B generate a magnetic field, which is opposite to the gradient magnetic field at the position of the optically pumped magnetometer 1A and has approximately the same magnitude as the gradient magnetic field, according to the current supplied from the coil power supply 6. The direction of the magnetic field is, for example, from one gradient magnetic field correction coil 8A to the other gradient magnetic field correction coil 8B. The gradient magnetic field at the position of the optically pumped magnetometer 1A is canceled by a magnetic field generated by the gradient magnetic field correction coil 8, the magnetic field being opposite to the gradient magnetic field and having approximately the same magnitude as the gradient magnetic field. In this manner, the gradient magnetic field correction coil 8 corrects the gradient magnetic field at the position of the optically pumped magnetometer 1A.

The active magnetic shield coil 9 is a coil for correcting the fluctuating magnetic field at the position of the optically pumped magnetometer 1A. The active magnetic shield coil 9 generates a magnetic field according to the current supplied from the coil power supply 6 to cancel the fluctuating magnetic field. The active magnetic shield coil 9 has, for example, a pair of active magnetic shield coils 9A and 9B. The pair of active magnetic shield coils 9A and 9B are arranged with the optically pumped magnetometer 1A interposed therebetween (for example, on the left and right of the subject). The pair of active magnetic shield coils 9A and 9B generate a magnetic field, which is opposite to the fluctuating magnetic field at the position of the optically pumped magnetometer 1A and has approximately the same magnitude as the fluctuating magnetic field, according to the current supplied from the coil power supply 6. The direction of the magnetic field is, for example, from one active magnetic shield coil 9A to the other active magnetic shield coil 9B. The fluctuating magnetic field at the position of the optically pumped magnetometer 1A is canceled by a magnetic field generated by the active magnetic shield coil 9, the magnetic field being opposite to the fluctuating magnetic field and having approximately the same magnitude as the fluctuating magnetic field. In this manner, the active magnetic shield coil 9 corrects the fluctuating magnetic field at the position of the optically pumped magnetometer 1A.

The pump laser 10 is a laser device that generates pump light. The pump light emitted from the pump laser 10 is incident on each of the multiple optically pumped magnetometers 1A by fiber branching.

The probe laser 11 is a laser device that generates probe light. The probe light emitted from the probe laser 11 is incident on each of the multiple optically pumped magnetometers 1A by fiber branching.

The amplifier 12 is a device or circuit that amplifies an output result signal from the OPM module 1 (specifically, the read circuit 1C) and outputs the signal to the control device 5.

The heater controller 13 is a temperature adjusting device connected to a heater (not shown) for heating the cell of the optically pumped magnetometer 1A and a thermocouple (not shown) for measuring the temperature of the cell. The heater controller 13 adjusts the temperature of each cell by receiving the temperature information of the cell from the thermocouple and adjusting the heating of the heater based on the temperature information.

The electromagnetic shield 14 is a shield member for shielding high-frequency (for example, 10 kHz or higher) electromagnetic noise. For example, the electromagnetic shield 14 is formed of a mesh woven with metal threads, a non-magnetic metal plate such as aluminum, or the like. The electromagnetic shield 14 is arranged so as to surround the optically pumped magnetometer 1A, the magnetic sensor for geomagnetic field correction 2, the magnetic sensor for active magnetic shield 3, the non-magnetic frame 4, the geomagnetic field correction coil 7, the gradient magnetic field correction coil 8, the active magnetic shield coil 9, and the bias magnetic field forming coil 15.

The bias magnetic field forming coil 15 is a coil for applying a bias magnetic field in the same direction as the direction of the pump light of each of the multiple pump-probe type optically pumped magnetometers 1A and in a direction approximately parallel to the scalp. The bias magnetic field forming coil 15 generates a bias magnetic field according to the current supplied from the coil power supply 6. The bias magnetic field forming coil 15 generates, for example, a bias magnetic field of 0.7 to 30 nT.

Figure 2A:
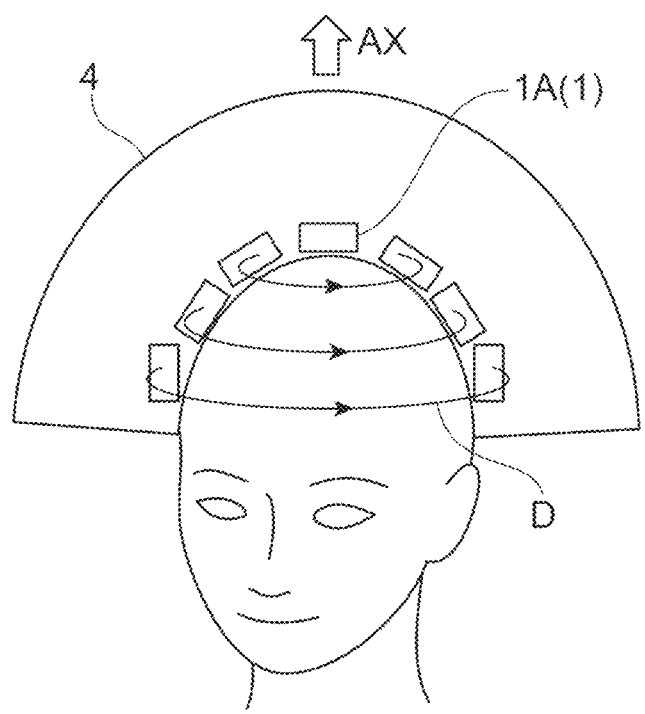
FIGS. 2A and 2B are schematic diagrams showing the direction of a bias magnetic field.
Figure 2B:
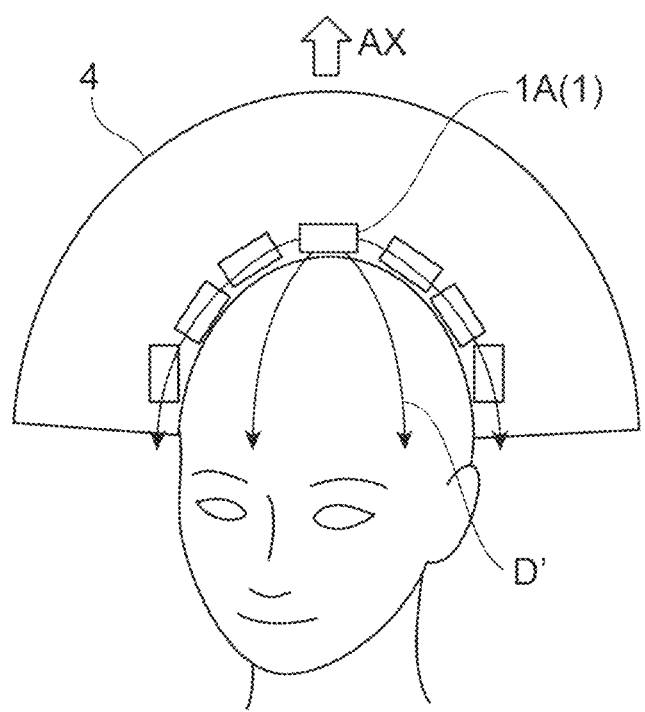

FIGS. 2A and 2B are schematic diagrams showing the direction of a bias magnetic field. FIGS. 2A and 2B show that the non-magnetic frame 4 is attached to the head of the subject. The direction of the bias magnetic field is a direction approximately parallel to the scalp of the subject (direction perpendicular to the brain's magnetic field generated in a vertical direction from the scalp). For example, as shown in FIG. 2A, the direction of the bias magnetic field is a direction D of each of concentric circles having a body axis AX of the subject as its center. The directions D of the concentric circles may be opposite directions. Such a bias magnetic field in the direction D of the concentric circles can be easily and stably applied. In addition, for example, as shown in FIG. 2B, the direction of the bias magnetic field may be a radial direction D' starting from the crown. The multiple optically pumped magnetometers 1A are arranged such that the direction of each pump light and the direction D or D' of the bias magnetic field are the same direction.

Figure 3:
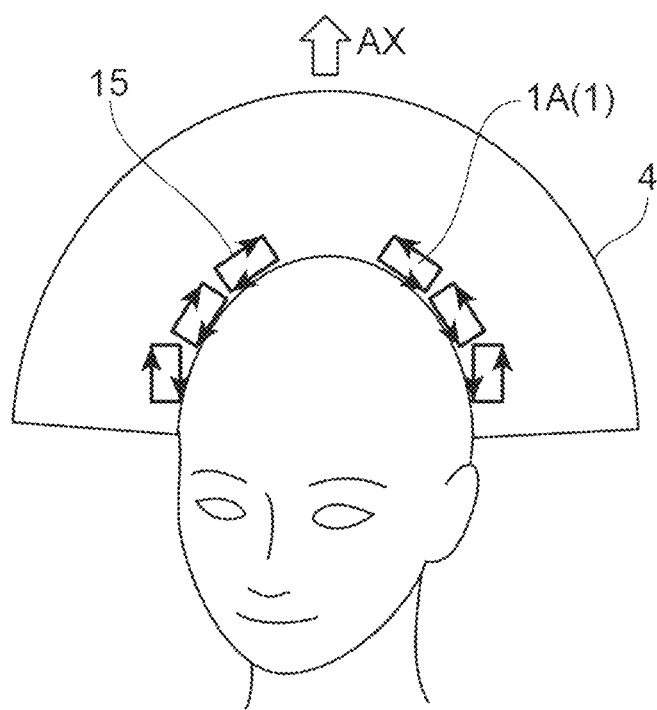
FIG. 3 is a schematic diagram showing an arrangement example of bias magnetic field forming coils.

FIG. 3 is a schematic diagram showing an arrangement example of the bias magnetic field forming coils 15. FIG. 3 shows that the non-magnetic frame 4 is attached to the head of the subject. In FIG. 3, the bias magnetic field forming coil 15 is a coil system arranged so as to individually surround each of the multiple pump-probe type optically pumped magnetometers 1A. The arrow indicated by the bias magnetic field forming coil 15 is the direction of the current. In order to avoid the influence of the bias magnetic field between the multiple optically pumped magnetometers 1A adjacent to each other, the multiple optically pumped magnetometers 1A may be arranged at fixed intervals. When the optically pumped magnetometer 1A is an axial gradiometer, the bias magnetic field forming coil 15 generates a bias magnetic field so that the magnetic field strength in the measurement region and the magnetic field strength in the reference region of the axial gradiometer are the same.

Figure 4:
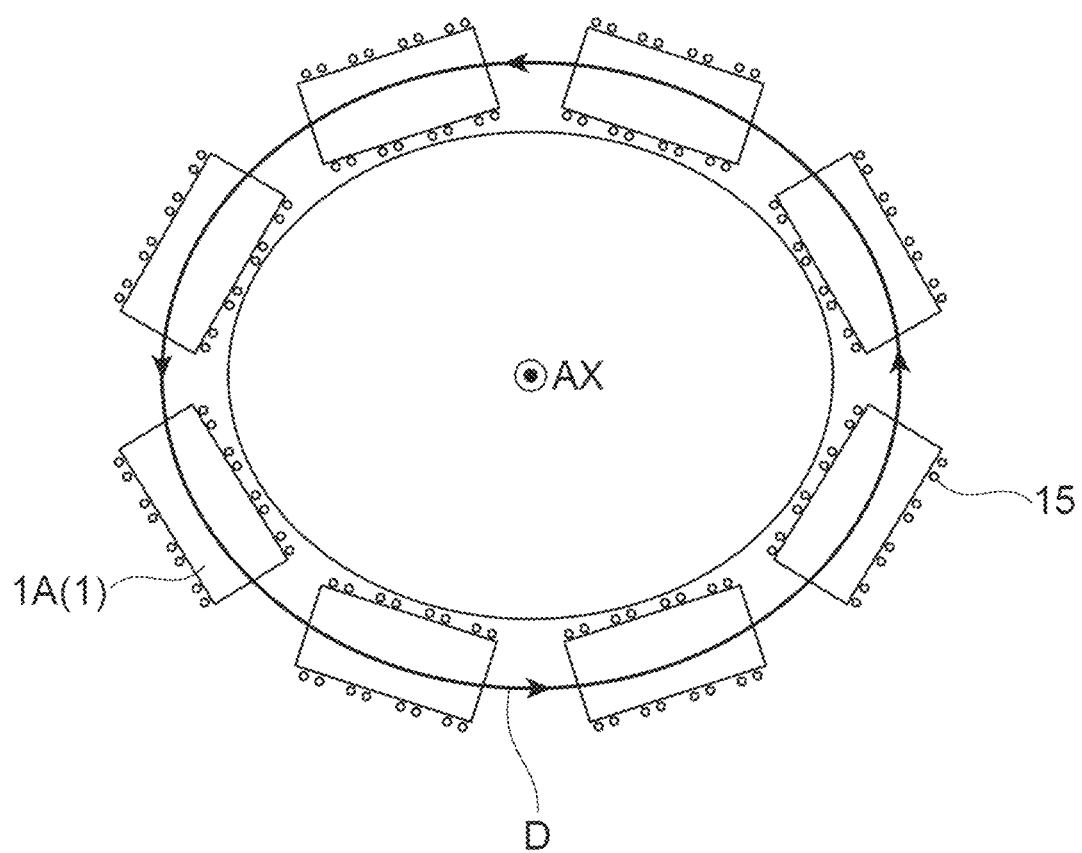
FIG. 4 is a schematic diagram showing the direction of a bias magnetic field according to the arrangement example of bias magnetic field forming coils.

FIG. 4 is a schematic diagram showing the direction of a bias magnetic field according to the arrangement example of the bias magnetic field forming coils 15. FIG. 4 is a diagram when the head of the subject is viewed from above the subject in the arrangement example shown in FIG. 3. The bias magnetic field forming coils 15 are arranged so as to individually surround each of the multiple optically pumped magnetometers 1A. However, for the sake of simplicity, only portions in contact with both ends of the optically pumped magnetometer 1A (OPM module 1) are shown. The direction of the bias magnetic field generated by the bias magnetic field forming coil 15 is the direction D of each of concentric circles having the body axis AX of the subject as its center. The directions D of the concentric circles may be opposite directions. The bias magnetic field forming coils 15 respectively arranged for the multiple optically pumped magnetometers 1A may cooperate with each other to apply a uniform bias magnetic field.

Figure 5:
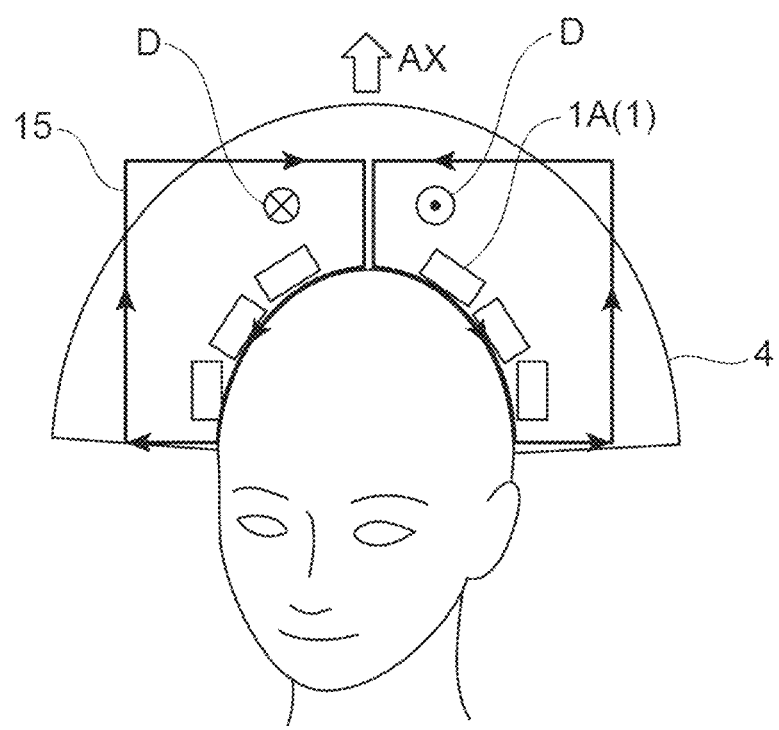
FIG. 5 is a schematic diagram showing another arrangement example of bias magnetic field forming coils.

FIG. 5 is a schematic diagram showing another arrangement example of the bias magnetic field forming coils 15. FIG. 5 shows that the non-magnetic frame 4 is attached to the head of the subject. In FIG. 5, the bias magnetic field forming coil 15 is a coil system arranged so as to surround at least two or more optically pumped magnetometers 1A included in the multiple pump-probe type optically pumped magnetometers 1A. The bias magnetic field forming coils 15 are spirally arranged around the head of the subject (for example, about 20 turns), and are connected in series to each other. In FIGS. 2A and 2B, for the sake of simplicity, only the coils for two turns are illustrated. The arrow indicated by the bias magnetic field forming coil 15 is the direction of the current. The direction of the bias magnetic field generated by the bias magnetic field forming coil 15 is the direction D of each of concentric circles having the body axis AX of the subject as its center. The directions D of the concentric circles may be opposite directions. The bias magnetic field forming coil 15 applies a uniform bias magnetic field to the multiple surrounding optically pumped magnetometers 1A.

Figure 6:
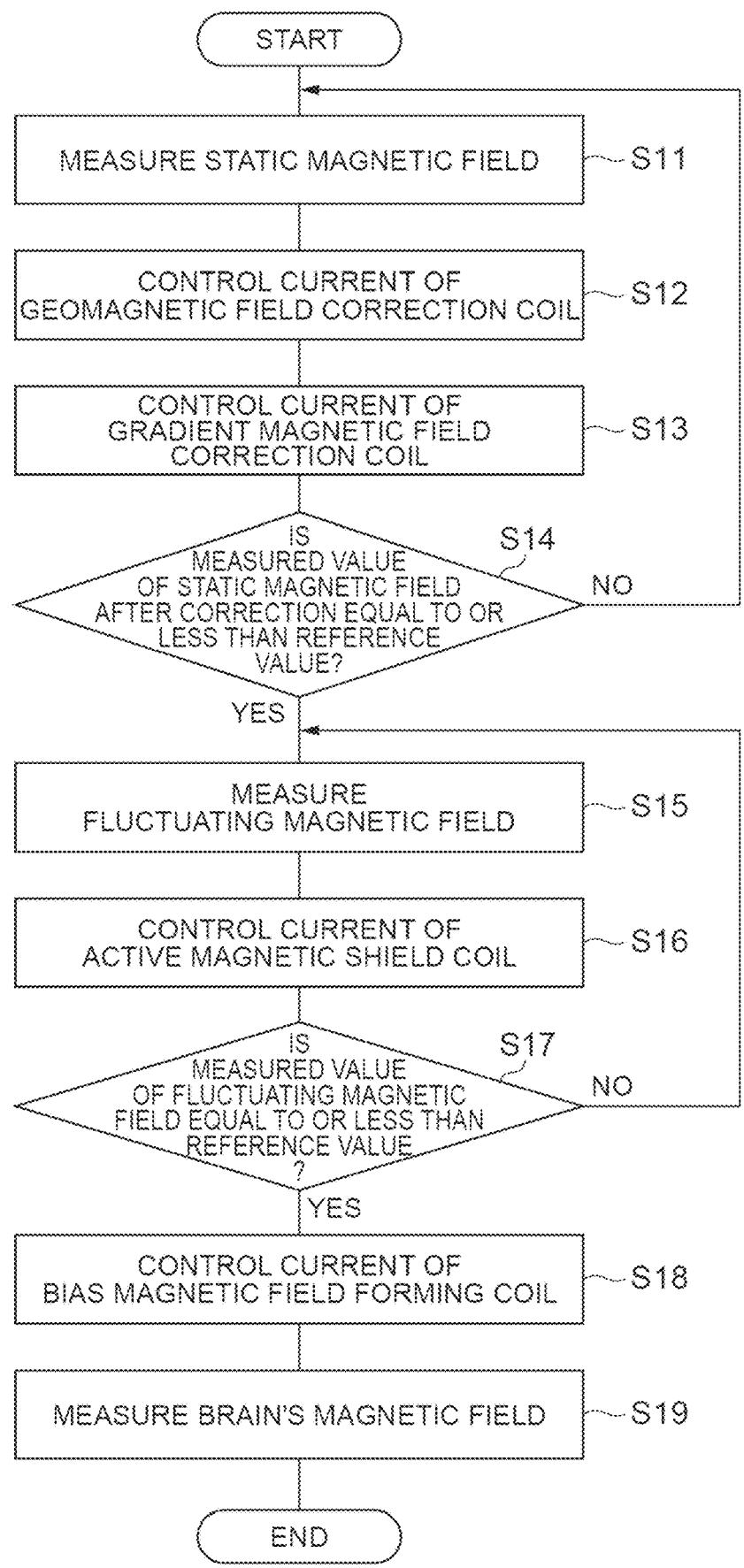
FIG. 6 is a flowchart showing the operation of the magnetoencephalograph according to the embodiment.

Next, a brain's magnetic field measurement method using the magnetoencephalograph M1 according to the embodiment will be described with reference to FIG. 6. FIG. 6 is a flowchart showing the operation of the magnetoencephalograph M1.

The magnetic sensor for geomagnetic field correction 2 measures a geomagnetic field, which is a static magnetic field (step S11). The magnetic sensor for geomagnetic field correction 2 measures the geomagnetism and the gradient magnetic field at each position of the optically pumped magnetometer 1A, and outputs the measured values to the control device 5.

The control device 5 and the coil power supply 6 control a current for the geomagnetic field correction coil 7 (step S12). The control device 5 determines a current for the geomagnetic field correction coil 7 based on the measured value of the magnetic sensor for geomagnetic field correction 2 so that a magnetic field opposite to the geomagnetism at the position of the optically pumped magnetometer 1A and having approximately the same magnitude as the geomagnetism is generated. More specifically, the control device 5 determines a current for the geomagnetic field correction coil 7 so that the average value of the measured values of the multiple magnetic sensors for geomagnetic field correction 2 approaches zero, for example. The control device 5 outputs a control signal corresponding to the determined current to the coil power supply 6. The coil power supply 6 outputs a predetermined current to the geomagnetic field correction coil 7 in response to the control signal output from the control device 5. The geomagnetic field correction coil 7 generates a magnetic field according to the current supplied from the coil power supply 6. The geomagnetism at the position of the optically pumped magnetometer 1A is canceled by a magnetic field generated by the geomagnetic field correction coil 7, the magnetic field being opposite to the geomagnetism and having approximately the same magnitude as the geomagnetism.

The control device 5 and the coil power supply 6 control a current for the gradient magnetic field correction coil 8 (step S13). The control device 5 determines a current for the gradient magnetic field correction coil 8 based on the measured value of the magnetic sensor for geomagnetic field correction 2 so that a magnetic field opposite to the gradient magnetic field at the position of the optically pumped magnetometer 1A and having approximately the same magnitude as the gradient magnetic field is generated. More specifically, the control device 5 determines a current for the gradient magnetic field correction coil 8 so that the deviation from the average value of the measured values of the multiple magnetic sensors for geomagnetic field correction 2 is minimized, for example. The control device 5 outputs a control signal corresponding to the determined current to the coil power supply 6. The coil power supply 6 outputs a predetermined current to the gradient magnetic field correction coil 8 in response to the control signal output from the control device 5. The gradient magnetic field correction coil 8 generates a magnetic field according to the current supplied from the coil power supply 6. The gradient magnetic field at the position of the optically pumped magnetometer 1A is canceled by a magnetic field generated by the gradient magnetic field correction coil 8, the magnetic field being opposite to the gradient magnetic field and having approximately the same magnitude as the gradient magnetic field.

The control device 5 determines whether or not the measured value of the static magnetic field (geomagnetic field) after the correction is equal to or less than the reference value (step S14). The measured value of the static magnetic field after the correction is a value measured by the magnetic sensors for geomagnetic field correction 2 after the static magnetic field is corrected by the geomagnetic field correction coil 7 and the gradient magnetic field correction coil 8. The reference value is the magnitude of the magnetic field in which the optically pumped magnetometer 1A normally operates, and can be set to, for example, 1 nT. If the measured value of the static magnetic field is not equal to or less than the reference value ("NO" in step S14), the process returns to step S11. If the measured value of the static magnetic field is equal to or less than the reference value ("YES" in step S14), the process proceeds to step S15.

The magnetic sensor for active magnetic shield 3 measures a fluctuating magnetic field (step S15). The magnetic sensor for active magnetic shield 3 measures a fluctuating magnetic field at each position of the optically pumped magnetometer 1A and outputs the measured value to the control device 5.

The control device 5 and the coil power supply 6 control a current for the active magnetic shield coil 9 (step S16). The control device 5 determines a current for the active magnetic shield coil 9 based on the measured value of the magnetic sensor for active magnetic shield 3 so that a magnetic field opposite to the fluctuating magnetic field at the position of the optically pumped magnetometer 1A and having approximately the same magnitude as the fluctuating magnetic field is generated. More specifically, the control device 5 determines a current for the active magnetic shield coil 9 so that the average value of the measured values of the multiple magnetic sensors for active magnetic shield 3 approaches zero, for example. The control device 5 outputs a control signal corresponding to the determined current to the coil power supply 6. The coil power supply 6 outputs a predetermined current to the active magnetic shield coil 9 in response to the control signal output from the control device 5. The active magnetic shield coil 9 generates a magnetic field according to the current supplied from the coil power supply 6. The fluctuating magnetic field at the position of the optically pumped magnetometer 1A is canceled by a magnetic field generated by the active magnetic shield coil 9, the magnetic field being opposite to the fluctuating magnetic field and having approximately the same magnitude as the fluctuating magnetic field.

The control device 5 determines whether or not the measured value of the fluctuating magnetic field after the correction is equal to or less than the reference value (step S17). The measured value of the fluctuating magnetic field after the correction is a value measured by the magnetic sensor for active magnetic shield 3 after the fluctuating magnetic field is corrected by the active magnetic shield coil 9. The reference value is a noise level at which the brain's magnetic field can be measured, and can be set to, for example, 1 pT. If the measured value of the fluctuating magnetic field is not less than or equal to the reference value ("NO" in step S17), the process returns to step S15. If the measured value of the fluctuating magnetic field is equal to or less than the reference value ("YES" in step S17), the process proceeds to step S18.

The control device 5 and the coil power supply 6 control a current for the bias magnetic field forming coil 15 (step S18). The control device 5 determines a current for the bias magnetic field forming coil 15 so as to generate a bias magnetic field for adjusting the resonance frequencies of the multiple pump-probe type optically pumped magnetometers 1A to be included in the frequency band of the brain's magnetic field. The control device 5 outputs a control signal corresponding to the determined current to the coil power supply 6. The coil power supply 6 outputs a predetermined current to the bias magnetic field forming coil 15 in response to the control signal output from the control device 5. The bias magnetic field forming coil 15 generates a bias magnetic field according to the current supplied from the coil power supply 6.

The optically pumped magnetometer 1A measures a brain's magnetic field (step S19). Since the static magnetic field (geomagnetic field) and the fluctuating magnetic field at the position of the optically pumped magnetometer 1A are canceled so as to be equal to or less than a predetermined reference value, the optically pumped magnetometer 1A can measure the brain's magnetic field in a state in which the influence of the static magnetic field (geomagnetic field) and the influence of the fluctuating magnetic field are avoided. In addition, each of the multiple optically pumped magnetometers 1A has a sensitivity suitable for measuring the brain's magnetic field. Therefore, it is possible to provide a magnetoencephalograph capable of performing measurement with high accuracy.

Operational Effects

Next, the operational effects of the magnetoencephalograph according to the above embodiment will be described.

The magnetoencephalograph M1 according to the present embodiment includes: multiple pump-probe type optically pumped magnetometers 1A that measure the brain's magnetic field; the bias magnetic field forming coil 15 for applying a bias magnetic field in the same direction as a direction of pump light of each of the multiple pump-probe type optically pumped magnetometers 1A and in a direction approximately parallel to the scalp; the control device 5 that determines a current for the bias magnetic field forming coil so as to generate a bias magnetic field for adjusting the resonance frequencies of the multiple pump-probe type optically pumped magnetometers to be included in the frequency band of the brain's magnetic field and outputs a control signal corresponding to the determined current; and the coil power supply 6 that outputs a current to the bias magnetic field forming coil in response to the control signal output from the control device.

In the magnetoencephalograph M1 according to the present embodiment, the bias magnetic field is applied in the same direction as the direction of the pump light of each of the multiple pump-probe type optically pumped magnetometers 1A and in the direction approximately parallel to the scalp, and the resonance frequencies of the multiple optically pumped magnetometers 1A are adjusted to be included in the frequency band of the brain's magnetic field. Since the brain's magnetic field is generated in the direction approximately perpendicular to the scalp, the bias magnetic field can be applied in a direction suitable for the brain's magnetic field by applying the bias magnetic field in the direction approximately parallel to the scalp and in the same direction as the direction of the pump light. Then, in the magnetoencephalograph M1 according to the present embodiment, since the resonance frequencies of the multiple optically pumped magnetometers 1A are adjusted to be included in the frequency band of the brain's magnetic field by the bias magnetic field, each of the multiple optically pumped magnetometers 1A is adjusted to have a sensitivity suitable for measuring the brain's magnetic field. As described above, according to the magnetoencephalograph M1 according to the present embodiment, the brain's magnetic field can be measured with high accuracy by appropriately adjusting the resonance frequency of each optically pumped magnetometer 1A.

A direction of the bias magnetic field may be a direction of each of concentric circles having a body axis of a subject as its center. Such a bias magnetic field in the direction of concentric circles can be easily and stably applied. Since the bias magnetic field is stable, it is possible to stably measure the brain's magnetic field.

The bias magnetic field forming coil 15 may be a coil system arranged so as to individually surround each of the multiple pump-probe type optically pumped magnetometers 1A. According to such a configuration, a bias magnetic field is applied to each of the multiple optically pumped magnetometers 1A. Therefore, a uniform bias magnetic field can be applied precisely.

The bias magnetic field forming coil 15 may be a coil system arranged so as to surround at least two or more optically pumped magnetometers 1A included in the multiple pump-probe type optically pumped magnetometers 1A. According to such a configuration, the bias magnetic field is collectively applied to two or more optically pumped magnetometers 1A surrounded by the bias magnetic field forming coil 15. Therefore, a uniform bias magnetic field can be efficiently applied with a simple configuration.

The multiple pump-probe type optically pumped magnetometers 1A may be axial gradiometers having a measurement region and a reference region in a direction perpendicular to the scalp and coaxially. According to such a configuration, since the influence of common mode noise is shown in each of the output result of the measurement region and the output result of the reference region, the common mode noise can be removed by acquiring the difference between the output results of both. As a result, the measurement accuracy of the brain's magnetic field is improved.

The magnetoencephalograph M1 according to the present embodiment may further include: multiple magnetic sensors for geomagnetic field correction 2 that measure a geomagnetic field at a position of each of the multiple pump-probe type optically pumped magnetometers 1A; multiple magnetic sensors for active magnetic shield 3 that measure a fluctuating magnetic field at the position of each of the multiple pump-probe type optically pumped magnetometers 1A; a geomagnetic field correction coil for correcting the geomagnetic field; and an active magnetic shield coil 9 for correcting the fluctuating magnetic field. The control device 5 may determine a current for the geomagnetic field correction coil so as to generate a magnetic field for canceling the geomagnetic field based on measured values of the multiple magnetic sensors for geomagnetic field correction 2, determine a current for the active magnetic shield coil 9 so as to generate a magnetic field for canceling the fluctuating magnetic field based on measured values of the multiple magnetic sensors for active magnetic shield 3, and output a control signal corresponding to each of the determined currents. The coil power supply 6 may further output a current to each of the geomagnetic field correction coil and the active magnetic shield coil 9 in response to the control signal output from the control device 5. According to such a configuration, the geomagnetic field and the fluctuating magnetic field at the position of each of the multiple optically pumped magnetometers 1A for measuring the brain's magnetic field are measured. Then, in this magnetoencephalograph M1, the current for the geomagnetic field correction coil is determined so as to generate a magnetic field for canceling the geomagnetic field based on the multiple measured values of the geomagnetic field, the current for the active magnetic shield coil 9 is determined so as to generate a magnetic field for canceling the fluctuating magnetic field based on the multiple measured values of the fluctuating magnetic field, and the control signal corresponding to each of the determined currents is output. Then, when the current corresponding to the control signal is output to each of the geomagnetic field correction coil and the active magnetic shield coil 9, a magnetic field is generated in each coil. At the positions of the multiple optically pumped magnetometers 1A, the geomagnetic field is canceled by the magnetic field generated in the geomagnetic field correction coil, and the fluctuating magnetic field is canceled by the magnetic field generated in the active magnetic shield coil 9. Therefore, since the geomagnetic field and the fluctuating magnetic field at the positions of the multiple optically pumped magnetometers 1A are canceled, the multiple optically pumped magnetometers 1A can measure the brain's magnetic field in a state in which the influence of the geomagnetic field and the influence of the fluctuating magnetic field are avoided. According to such a magnetoencephalograph M1, the brain's magnetic field can be measured with high accuracy without using the magnetic shield room.

The multiple pump-probe type optically pumped magnetometers 1A, the multiple magnetic sensors for geomagnetic field correction 2, and the multiple magnetic sensors for active magnetic shield 3 may be fixed to the non-magnetic frame 4 which is a helmet-type frame attached to the head of a subject and whose relative permeability is close to 1 so that the magnetic field distribution is not affected. According to such a configuration, the non-magnetic frame 4 attached to the head and each sensor fixed to the non-magnetic frame 4 move according to the movement of the head of the subject. Therefore, even when the head of the subject moves, it is possible to appropriately correct the geomagnetic field and the fluctuating magnetic field at the positions of the multiple optically pumped magnetometers 1A and measure the brain's magnetic field.

The electromagnetic shield 14 for shielding high-frequency electromagnetic noise may be further provided. According to such a configuration, it is possible to prevent high-frequency electromagnetic noise, which cannot be measured by the magnetoencephalograph M1, from entering the multiple optically pumped magnetometers 1A. As a result, the multiple optically pumped magnetometers 1A can be stably operated.

What is claimed is:

1. A magnetoencephalograph, comprising:
   multiple pump-probe type optically pumped magnetometers configured to measure a brain's magnetic field;
   a bias magnetic field forming coil for applying a bias magnetic field in the same direction as a direction of pump light of each of the multiple pump-probe type optically pumped magnetometers and in a direction approximately parallel to a scalp;
   a control device configured to determine a current for the bias magnetic field forming coil so that the bias magnetic field forming coil generates a bias magnetic field for adjusting resonance frequencies of the multiple pump-probe type optically pumped magnetometers to be included in a frequency band of the brain's magnetic field and output a control signal corresponding to the determined current; and
   a coil power supply configured to output a current to the bias magnetic field forming coil in response to the control signal output from the control device.

2. The magnetoencephalograph according to claim 1, wherein a direction of the bias magnetic field is a direction of each of concentric circles having a body axis of a subject as its center.

3. The magnetoencephalograph according to claim 1, wherein the bias magnetic field forming coil is a coil system arranged to individually surround each of the multiple pump-probe type optically pumped magnetometers.

4. The magnetoencephalograph according to claim 1, wherein the bias magnetic field forming coil is a coil system arranged to surround at least two or more optically pumped magnetometers included in the multiple pump-probe type optically pumped magnetometers.

5. The magnetoencephalograph according to claim 1, wherein the multiple pump-probe type optically pumped magnetometers are axial gradiometers having a measurement region and a reference region in a direction perpendicular to the scalp and coaxially.

6. The magnetoencephalograph according to claim 1, further comprising:
   multiple magnetic sensors for geomagnetic field correction configured to measure a geomagnetic field at a position of each of the multiple pump-probe type optically pumped magnetometers;
   multiple magnetic sensors for active magnetic shield configured to measure a fluctuating magnetic field at the position of each of the multiple pump-probe type optically pumped magnetometers;
   a geomagnetic field correction coil for correcting the geomagnetic field; and
   an active magnetic shield coil for correcting the fluctuating magnetic field,
   wherein the control device determines a current for the geomagnetic field correction coil so that the geomagnetic field correction coil generates a magnetic field for canceling the geomagnetic field based on measured values of the multiple magnetic sensors for geomagnetic field correction, determines a current for the active magnetic shield coil so that the active magnetic shield coil generates a magnetic field for canceling the fluctuating magnetic field based on measured values of the multiple magnetic sensors for active magnetic shield, and outputs a control signal corresponding to each of the determined currents, and
   the coil power supply further outputs a current to each of the geomagnetic field correction coil and the active magnetic shield coil in response to the control signal output from the control device.

7. The magnetoencephalograph according to claim 6, wherein the multiple pump-probe type optically pumped magnetometers, the multiple magnetic sensors for geomagnetic field correction, and the multiple magnetic sensors for active magnetic shield are fixed to a non-magnetic frame of helmet-type attached to a head of a subject and having a relative permeability close to 1 so that a magnetic field distribution is not affected.

8. The magnetoencephalograph according to claim 6, further comprising:
   an electromagnetic shield for shielding high-frequency electromagnetic noise.

* * * * *